United States Patent [19]

Hosoi et al.

[11] Patent Number: 5,513,987
[45] Date of Patent: May 7, 1996

[54] DENTURE, METHOD OF REPAIRING DENTURE AND DENTAL SOFT RELINING MATERIAL USED THEREFOR

[75] Inventors: Yasuhiro Hosoi; Osamu Iwamoto; Masataka Himeno, all of Tokuyama, Japan

[73] Assignee: Tokuyama Soda Kabushiki Kaisha, Tokuyama, Japan

[21] Appl. No.: 207,168

[22] Filed: Mar. 8, 1994

[30] Foreign Application Priority Data

| Mar. 9, 1993 | [JP] | Japan | 5-047779 |
| May 11, 1993 | [JP] | Japan | 5-108999 |
| May 21, 1993 | [JP] | Japan | 5-118887 |
| Nov. 29, 1993 | [JP] | Japan | 5-297728 |
| Dec. 2, 1993 | [JP] | Japan | 5-302669 |

[51] Int. Cl.$^6$ .................................. A61C 13/02
[52] U.S. Cl. ........................ 433/168.1; 433/199.1
[58] Field of Search ........................ 433/167, 168.1, 433/171, 199.1; 427/2.29, 387

[56] References Cited

U.S. PATENT DOCUMENTS

| 5,112,640 | 5/1992 | Warunek et al. | 427/2 |
| 5,346,932 | 9/1994 | Takahashi et al. | 523/213 |

FOREIGN PATENT DOCUMENTS

| 0046907 | 8/1981 | European Pat. Off. . |
| 2178329 | 10/1973 | France . |
| 3902817 | 8/1989 | Germany . |

OTHER PUBLICATIONS

Patent Abstracts of Japan, JP-A-61 159 50.
Patent Abstracts of Japan, JP-A-58 201 707.
Patent Abstract, SU-A0952 914, Derwent Publications Ltd., London, GB.

*Primary Examiner*—Cary E. O'Connor
*Attorney, Agent, or Firm*—Sherman and Shalloway

[57] ABSTRACT

A denture having a layer of a soft relining material and a method of repairing denture. The denture has on the mucosa surface thereof the soft relining material which comprises a cured product of a composition that contains (A) 100 parts by weight of an organopolysiloxane having in a molecule thereof at least two organic groups with a terminal unsaturated bond, (B) an organohydrogenpolysiloxane having in a molecule thereof at least three hydrogen atoms bonded to silicon atoms, in such an amount that the number of said hydrogen atoms is 0.5 or greater per one unsaturated bond in the component (A), (C) a platinum catalyst in an amount of 0.1 to 1000 ppm reckoned as platinum atoms with respect to the total amount of the component (A) and the component (B), and (D) 5 to 300 parts by weight of a fine particle of a polyorganosilsesquioxane.

17 Claims, No Drawings

DENTURE, METHOD OF REPAIRING DENTURE AND DENTAL SOFT RELINING MATERIAL USED THEREFOR

BACKGROUND OF THE INVENTION

1. Field of the Invention

The present invention relates to a denture provided with a layer of a soft relining material and to a method of repairing the denture. The invention further relates to a dental soft relining material used for such applications.

2. Description of the Prior Art

Patients who need a denture and, particularly, a full denture, in many cases, are aged persons, and their alveolar ridges must bear an increased occlusion force per a unit area since the bone has generally been resorbed to a conspicuous degree. The mucosa of alveolar ridge becomes thin due to senile atrophy, and the occlusion stress or masticatory pressure is not softened but is directly transmitted to the alveolar bone. Moreover, a thin mucosa disposed between a hard resin denture base and the hard alveolar bone is tightened and gets hurt after every occlusion, and begins to feel pain.

In such a serious case, the resin denture base molded by using a methyl methacrylate resin that is usually used is not sufficient for stably maintaining the mastication and supporting the adhesion of the denture. That is, it is necessary to reline the mucosa surface of the resin denture base with a soft dental relining material to compensate the lost viscoelasticity of the mucosa of the residual alveolar ridge, in order to impart cushioning property that softens the occlusal stress. That is, the object of relining with a soft material is to overcome various troubles that develop when the thin mucosa is compressed by the hard denture base.

Dental soft relining materials used, so far, for the clinic include a (meth)acrylic acid ester polymer, a fluorine-containing resin, a polyolefin type resin, a silicone rubber, and the like. For temporary applications, furthermore, there is used a denture adhesive.

However, the soft material such as the (meth)acrylic acid polymer or the like lacks chemical stability in the oral cavity, become hard and brittle within several months, and are not usable for extended periods of time. The fluorine type relining material lacks viscoelasticity from which sufficient cushioning effect cannot be expected. The polyolefin type relining material has many problems from a practical point of view. That is, it may deform the resin denture base because the preparation temperature is high, and it requires a plurality of adhesives and a special heating device, involving a cumbersome operation. The silicone rubber-type relining material is relatively stable but is not sufficient in regard to durability, especially straining, and operability, especially trimming. In particular, the soft relining materials that are now used in the clinic do not almost have machinability and cannot be corrected once they are cured.

Even as for the denture adhesive, the consistency increases as it is used for extended periods of time and the plasticity decreases. As a result, the fit and marginal shut of ill-fitting denture are not improved and, hence, the object of enhancing the stability and support of the denture base is not fully accomplished and, besides, the oral tissue is damaged in many cases. Moreover, since the denture has a small compressive stress and lacks elasticity, its cushioning effect is not sufficient for the occlusal stress and that becomes a cause of the recurrence of pain in the oral mucosa.

As described above, the dental soft relining material for denture base provided so far lost physical properties after the use of a short period of time, could be used in the oral cavity for only a short period of time, could not offer satisfactory cushioning effect, could be used requiring cumbersome method, and was not practicable. It has therefore been desired to provide a soft relining material for dental use having a suitable viscoelasticity, without losing physical properties, and having excellent operability and, particularly, machinability. In particular, the soft relining material for dental use having such properties is strongly demanded toward the coming aging society.

SUMMARY OF THE INVENTION

The present inventors have conducted a keen study in order to solve the above-mentioned problems inherent in the prior art, and have developed a soft relining material for dental use that exhibits excellent durability and operability and can be used for extended periods of time by using a silicone rubber as a matrix and particles fine particle of a polyorganosilsesquioxane as a filler.

That is, the present invention is concerned with a dental soft relining material containing:

(A) 100 parts by weight of an organopolysiloxane having in a molecule thereof at least two organic groups with a terminal unsaturated bond;

(B) an organohydrogenpolysiloxane having in a molecule thereof at least three hydrogen atoms bonded to silicon atoms, in such an amount that the number of said hydrogen atoms is 0.5 or greater per one unsaturated bond in the component (A);

(C) a platinum catalyst in an amount of 0.1 to 1000 ppm reckoned as platinum atoms with respect to the total amount of the component (A) and the component (B); and (D) 5 to 300 parts by weight of particles fine particle of a polyorganosilsesquioxane.

The present invention is further concerned with a dental soft relining material containing:

(E) 100 parts by weight of an organopolysiloxane;

(F) 0.05 to 15 parts by weight of an organic peroxide; and (D) 5 to 300 parts by weight of fine particles of polyorganosilsesquioxane.

According to the present invention, furthermore, there is provided a denture comprising a denture and a layer of a soft relining material provided on the side of the mucosa surface of the denture, the soft relining material comprising a cured product of a composition of said components (A), (B), (C) and (D) or a cured product of a composition of said components (E), (F) and (D).

According to a further aspect of the present invention, there is provided a method of repairing denture by applying a relining material containing the above components (A), (B), (C) and (D) or a relining material containing the above components (E), (F) and (D) onto the mucosa surface of the denture and/or onto an alveolar model, adhering the denture with force to the residual ridge or to the alveolar model, and curing said relining material.

The denture is adhered with force to the alveolar model when said relining material comprises a composition of the components (E), (F) and (D).

DETAILED DESCRIPTION OF PREFERRED EMBODIMENTS

Relining Material (I)

The organopolysiloxane (A) having in a molecule thereof at least two organic groups with a terminal unsaturated bond (hereinafter abbreviated as unsaturated bond-containing silicone) is a main component which forms a rubbery elastic material upon crosslinking by hydrosilation reaction with the organohydrogenpolysiloxane (B) (hereinafter abbreviated as SiH siloxane).

The unsaturated bond-containing silicone which is the component (A) has no limitation on the structure of other organic groups, and may be of the type of a linear chain, a branched chain or a mixture thereof provided it is an organopolysiloxane having in a molecule thereof at least two organic groups with a terminal unsaturated bond.

Examples of the organic group having a terminal unsaturated bond includes a vinyl group, an allyl group, a 1-butenyl group, etc. From the standpoint of easy synthesis, however, the vinyl group bonded to silicon atom is most advantageously used. The organic groups having the terminal unsaturated bond may exist at the terminals or at intermediate positions of the molecular chain of the organosiloxane or at both of them. In order that the elastic material after being cured exhibits excellent physical properties, however, at least one of the organic groups should exist at a terminal.

Examples of the organic group bonded to silicon atom other than the organic groups having a terminal unsaturated bond include alkyl groups such as a methyl group, an ethyl group, a propyl group, a butyl group and an octyl group, aryl groups such as a phenyl group, etc., and substituted alkyl groups such as a chloromethyl group, a 3,3,3-trifluoropropyl group, etc. Among them, however, the methyl group is most preferred since it can be easily synthesized and maintains favorable physical properties after being cured.

In order to obtain the dental soft relining material, furthermore, it is desired that siloxane units consisting of organic groups only without terminal unsaturated bond are contained in a number of 50 to 5000 and, particularly, in a number of 100 to 2000 continuously between the siloxane units consisting of organic groups having a terminal unsaturated bond, so that properties suited for the dental soft relining materials are obtained and, particularly, so that a suitable degree of hardness is obtained after curing and that a sufficient elongation and mechanical strength are obtained. When the number of siloxane units consisting only of the organic groups without terminal unsaturated bond is smaller than 50, it becomes difficult to obtain a sufficient degree of elongation, elasticity or mechanical strength. When the number of siloxane units consisting only of organic groups without terminal unsaturated bond is greater than 5000, the viscosity becomes too great, the operability before being cured is impaired, and sufficient degree of hardness is not obtained after curing.

Concrete examples of the silicone containing unsaturated bonds used in the present invention are as follows:

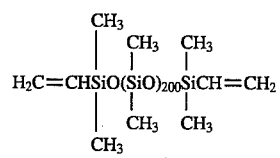

(1)

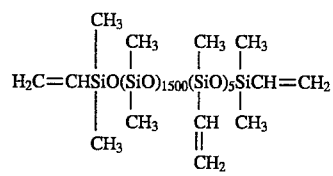

(2)

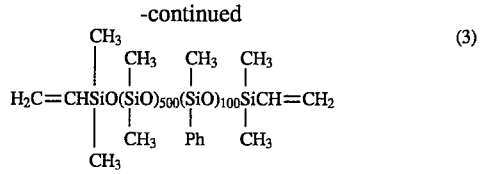

(3)

wherein Ph is a phenyl group.

In the above-mentioned compounds and in the compounds used in Examples and Comparative Examples appearing later, the order of bonding the recurring constituent units is quite arbitrary, and the numbers of recurring constituent units shown in the structural formulas merely represent average total weights of the constituent units.

The SiH siloxane which is the component (B) of the present invention works to form a rubbery elastic material upon crosslinking by hydrosilation reaction with the silicone having unsaturated bond. In order to obtain the crosslinked structure upon the reaction with the silicone having unsaturated bond, it is necessary that each molecule has at least three hydrogen atoms bonded to silicon atoms.

The organic groups bonded to silicon atoms other than hydrogen atoms will be the same as the organic groups having a terminal unsaturated bond in the above-mentioned component (A) and the organic groups without terminal unsaturated bond. However, the methyl group is most preferably used from the standpoint of easy synthesis and maintaining favorable physical properties after curing. The SiH silicone may be of the type of a linear chain, a branched chain, an annular chain or a mixture thereof.

Concrete examples of the SiH siloxane used in the present invention are as follows:

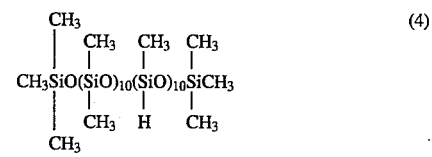

(4)

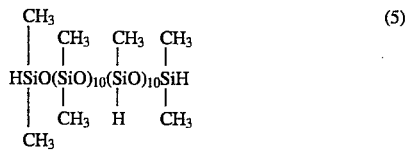

(5)

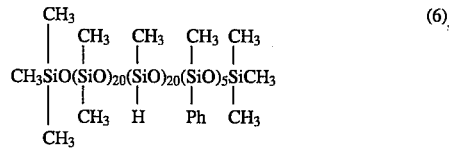

(6)

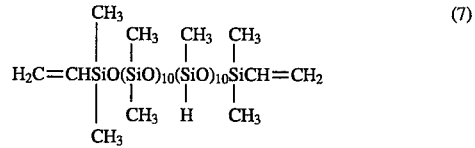

(7)

(8)

Even in the above-mentioned SiH siloxane and in the SiH siloxanes used in Examples and Comparative Examples appearing later, it should be noted that the order of bonding the recurring constituent units in the molecules is quite arbitrary like in the silicone containing unsaturated bond, and the numbers of the recurring constituent units in the structural formulas merely represent average total numbers of the constituent units.

According to the present invention, the amounts of blending the silicone having an unsaturated bond and the SiH siloxane vary depending upon the molecular weights. Usually, however, they are blended in such a ratio that the number of hydrogen atoms bonded to silicon atoms in the SiH siloxane is 0.5 or greater and, preferably, 1 to 5 per one unsaturated bond in the unsaturated bond-containing silicone. When this ratio is too small, the curing is not effected sufficiently. When this ratio is too great, on the other hand, the obtained elastic material becomes brittle or hydrogen atoms bonded to silicon atoms remain in excess amounts, causing the elastic material to lose stability with the passage of time.

When the number of hydrogen atoms bonded to silicon atoms is 0.5 or larger per one unsaturated bond in the unsaturated bond-containing silicone owing to the organohydrogenpolysiloxane that has in a molecule thereof at least three hydrogen atoms bonded to silicon atoms, then it is allowable to further add an organohydrogenpolysiloxane that has in a molecule thereof only two or one hydrogen atom bonded to silicon atoms.

Any platinum catalyst can be used as the component (C) of the present invention provided it is the one that is used for the ordinary hydrosilation reaction, such as platinum, chloroplatinic acid, an alcohol-modified product thereof, a vinyl siloxane complex of platinum, and the like. In order to enhance the preservation property, it is desired to use, for example, the vinyl siloxane complex of platinum having a small chlorine component, which is prepared by a process disclosed in, for example, U.S. Pat. No. 3,775,452.

The platinum catalyst should be blended in an amount of from 0.1 to 1000 ppm reckoned as platinum atoms with respect to the total weight of the unsaturated bond-containing silicone and the SiH siloxane. When the blending amount is smaller than 0.1 ppm, the crosslinking reaction does not sufficiently proceed between the unsaturated bond-containing silicone and the SiH siloxane. When the blending amount is larger than 1000 ppm, on the other hand, platinum black precipitates causing the cured product to be colored in yellow or, in an extreme case, in black, and making it difficult to control the crosslinking reaction.

The fine particles of a polyorganosilsesquioxane which is the component (D) used in the present invention works as a reinforcing material for the silicone rubber obtained from the component (A), component (B) and component (C).

Silica-type powder such as pulverized quartz, fused silica, colloidal silica or fumed silica is generally effectively used as a reinforcing material for the silicone rubber. For the dental soft relining material, however, the silanol group that remains in the grains and/or on the surfaces of the grains causes these silica-type powders to become highly hydrophilic, leaving a defect of coloring (hereinafter abbreviated as the amount of coloring) due to the infiltration of coloring component from the elastic material after being cured. Moreover, the fine powder such as of colloidal silica or fumed silica is not capable of imparting sufficient rigidity to the elastic material after being cured since the grain size is too small. Therefore, the elastic material does not exhibit good machinability. As a filler having a low hydrophilic property, there can be used a fluorocarbon resin powder such as of a polytetrafluoroethylene, a polyvinylidene fluoride, etc. They, however, exhibit a small reinforcing effect for the silicone rubber. Moreover, compatibility is poor between the fluorocarbon resin and the silicone rubber, and the matrix/filler interface is not so intimate that the formation of voids induces infiltration of a coloring component thereinto. Therefore, the amount of coloring is large despite a small hydrophilic property of the filler.

However, the filler which is the component (D) used in the present invention, i.e., the fine particles of polyorganosilsesquioxane, has a large hydrophobic property compared with the aforementioned silica-type powder and, further, has an Si—O bond and an Si—CH$_3$ bond, and exhibits intimacy to the silicone which is the matrix and further exhibits increased reinforcing effect for the silicone rubber. Therefore, the elastic material after being cured has a sufficient mechanical strength and, at the same time, a small amount of coloring. By selecting a suitable degree of grain size, furthermore, the filler can be charged at a high charging rate and, besides, a sufficient rigidity can be imparted to the elastic material after curing. Accordingly, machinability is imparted to the elastic material after curing.

As the fine particles of a polyorganosilsesquioxane of the present invention, there can be used a widely known fine powdery of a polyorganosilsesquioxane. As the organic groups of the fine particles of a polyorganosilsesquioxane, there can be exemplified alkyl groups such as a methyl group, an ethyl group, a propyl group, a butyl group and an octyl group, alkylene groups such as a vinyl group, an allyl group and a 1-butenyl group, aryl groups such as a phenyl group, etc., substituted alkyl groups such as a chloromethyl group, a 3,3,3-trifluoropropyl group, etc., as well as a hydrogen atom and the like. Among them, the methyl group or the methyl group and the one in which a portion thereof is substituted by the above-mentioned organic group, can be favorably used from the standpoint of easy synthesis and maintaining good physical properties after curing.

Concrete examples of the polyorganopolysilsesquioxane used in the present invention include a polymethylsilsesquioxane, a poly (50 mol % methyl+50 mol % phenyl) silsesquioxane, a poly (99 mol % methyl+1 mol % hydrogen) silsesquioxane, etc.

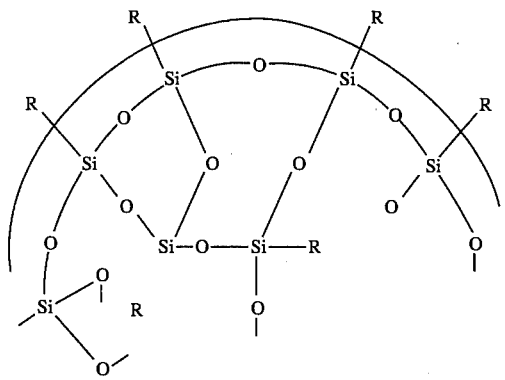

R: methyl group
polymethylsilsesquioxane.

A hydrolyzed product of a methyltrialkoxysilane.

Japanese Laid-Open Patent Publication No. 159450/1986 discloses fine particles of a polyorganosilsesquioxane and particularly fine particles of a polymethylsilsesquioxane as a filler for the silicone rubber composition. This Japanese Laid-Open Patent Publication No. 159450/1986, however, merely refers to the parting property and the peeling property and teaches the use of the compound simply as a parting material and a peeling material. The present inventors, however, have discovered the fact that the above-mentioned composition exhibits excellent resistance against coloring and has sufficient strength and machinability, and have attempted to use it as a dental soft relining material.

Preferably, the fine particles of a polyorganosilsesquioxane is obtained by hydrolyzing and condensing the organotrialkoxysilane or a mixture of one or more kinds of the hydrolyzed products thereof and condensed products thereof in an aqueous solution of ammonia or amines, without almost containing impurities such as chlorine atoms, alkaline earth metals or alkali metals and having a spherical shape.

The fine particles of a polyorganosilsesquioxane have an average grain size of from 0.1 to 100 μm and, preferably, from 0.1 to 20 μm. When the grain size is smaller than 0.1 μm, the fine particles of a polyorganosilsesquioxane is produced with difficulty and cannot be charged in an amount sufficient to obtain a dental soft relining material. When the grain size exceeds 100 μm, on the other hand, it becomes difficult to obtain reinforcing effect; i.e., it becomes difficult to obtain the dental soft relining material having necessary reinforcing effect.

The fine particles must be blended in an amount of from 5 to 900 parts by weight per 100 parts by weight of the unsaturated bond-containing silicone which is the component (A). When the amount is smaller than 5 parts by weight, the elastic material after curing does not exhibit sufficient mechanical strength. When the amount is greater than 300 parts by weight, on the other hand, the fine particles are not well blended in the system and fail to form a paste. Moreover, the elastic material after curing lacks rubbery elasticity, loses reinforcing effect, and exhibits deteriorated mechanical strength.

According to the present invention, the dental soft relining material may, as required, be blended with any filler other than the fine particles of a polyorganosilsesquioxane in such an amount that does not drastically deteriorate the properties thereof. Representative examples of the filler include silica type powders such as of a pulverized quartz, a molten silica, a wet silica and a dry silica, fluorocarbon resin powders such as of a polytetrafluoroethylene and a polyvinylidene fluoride, as well as carbon black, a glass fiber, a pulverized polymer, a powdery polymer, a composite filler (a pulverized composite of an inorganic oxide and a polymer) and the like.

It is also allowable to add any other additives within a range that does not drastically deteriorate the properties. Examples of the additive include a nonreactive silicone, a reaction suppressing agent, an ultraviolet-ray absorbing agent, a plasticizer, a pigment, an antioxidizing agent, an antibacterial agent and the like.

According to the present invention, the dental soft relining material is prepared in two packages of an agent A containing a filler comprising chiefly an unsaturated bond-containing silicone and fine particles of a polyorganosilsesquioxane and further containing a platinum catalyst and, as required, additives, and an agent B containing a filler comprising chiefly an SiH siloxane and fine particles of a polyorganosilsesquioxane and further containing, as required, the unsaturated bond-containing silicone and additives. The two packages are usually mixed together just before being used.

The method of preparation consists of measuring suitable amounts of the unsaturated bond-containing silicone, SiH siloxane, fine particles of a polyorganosilsesquioxane, platinum catalyst, filler other than the fine particles of a polyorganosilsesquioxane and required components out of the additives, and kneading them together by using a general kneading machine such as a kneader or a planetary to obtain a homogeneous paste-like composition.

Relining material (II)

The organopolysiloxane which is the component (E) used in another composition of the present invention is the one that is used for an ordinary silicone rubber, and may be of the type of a straight chain, a branched chain, or a mixture thereof. The organic groups bonded to silicon atoms in the diorganosiloxy unit which is a recurring unit may be alkyl groups such as a methyl group, an ethyl group, a propyl group, a butyl group or an octyl group, alkylene groups such as a vinyl group, an allyl group or a 1-butenyl group, aryl groups such as a phenyl group, or substituted alkyl groups such as a chloromethyl group or a 3,3,3-trifluoropropyl group. From the standpoint of easy synthesis and maintaining favorable physical properties after being cured, however, it is desired to use the methyl group, the vinyl group or a mixture thereof. In the triorganosiloxy unit which is the terminal unit of the organopolysiloxane, furthermore, the organic groups bonded to silicon atoms may be any combination of the above-mentioned organic groups. It is, however, desired to use a dimethylvinylsiloxy unit and a trimethylsiloxy unit from the standpoint of easy synthesis and crosslinking reaction.

It is desired that the organopolysiloxane which is the component (E) has a number of siloxy units, i.e., an average polymerization degree of from 50 to 5000 and, particularly, from 100 to 2000. When the average polymerization degree is smaller than 50, it becomes difficult to obtain sufficient elasticity, elongation or mechanical strength after cured. When the average polymerization degree exceeds 5000, on the other hand, the viscosity becomes too high, the operability before the curing is impaired and, besides, it becomes difficult to obtain a sufficient mechanical strength after the curing.

Representative examples of the organopolysiloxane used in the present invention are concretely shown below.

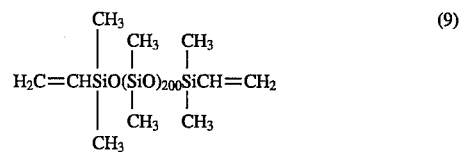

(9)

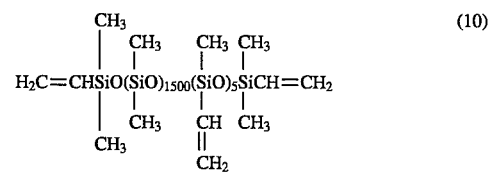

(10)

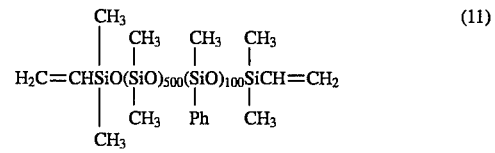

(11)

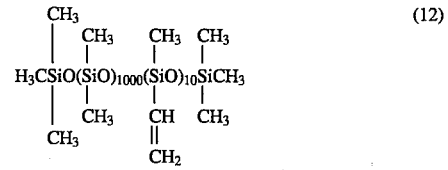

(12)

wherein Ph denotes a phenyl group.

It should be noted here that in the above-mentioned compounds and in the compounds used in Examples and Comparative Examples appearing later, the order of bonding the recurring constituent units is quite arbitrary, and the numbers of recurring constituent units shown in the structural formulas merely represent average total weights of the constituent units.

The organic peroxide which is the component (F) used in the composition (II) of the present invention is a vulcanizing agent for vulcanizing and curing the organopolysiloxane which is the component (E), and has heretofore been used for vulcanizing the thermosetting silicone rubbers. Examples of the organic peroxide include acyl-type peroxides such as a benzoyl peroxide and a p-chlorobenzoyl peroxide, and nonacyl-type peroxides such as a di-t-butyl peroxide, a 2,5-dimethyl-2,5-di(t-butylperoxy) hexane and a dicumyl peroxide. The organic peroxides may be used in the form of a mixture of one or two or more kinds. The organic peroxide which is the component (F) is blended in an amount over a range of from 0.05 to 15 parts by weight per 100 parts by weight of the organopolysiloxane which is the component (E). When the organic peroxide which is the component (F) is blended in an amount of smaller than 0.05 parts by weight, the vulcanization is not sufficiently effected. When the organic peroxide is blended in an amount greater than 15 parts by weight, no particularly distinguished effect is obtained and, besides, the properties of the obtained silicone rubber elastic material are adversely affected.

The fine particles of a polyorganosilsesquioxane which is the component (D) used in the composition (II) of the present invention is the one that was mentioned in detail already in connection with the composition (I).

Because of the same reasons as described above, the component (D) is blended in an amount of from 5 to 300 parts by weight per 100 parts by weight of the organopolysiloxane which is the component (E).

The composition (II) of the present invention may also be blended with the fillers and additives that were mentioned in connection with the relining material (I).

According to the present invention, the dental soft relining material (II) is obtained in the form of a paste-like composition by measuring suitable amounts of the organopolysiloxane, organic peroxide, fine particles of a polyorganosilsesquioxane, filler other than the fine particles of a polyorganosilsesquioxane and required components out of the additives, and kneading them together by using a general kneading machine such as a kneader or a planetary until the mixture becomes homogeneous.

Method of repairing denture

The repairing method using the dental soft relining material (I) of the present invention can be roughly divided into two, i.e., a direct method and an indirect method. According to the direct method, a portion to be relined with the soft relining material is cut off. Then, the two kinds of pastes A and B are measured in suitable amounts, mixed together, and are applied onto the relining portion of the denture. The denture is then directly fitted into the oral cavity of a patient and is held until the pastes are sufficiently cured. After being cured, the denture is taken out from the oral cavity and excess portions are removed by cutting. According to the indirect method, on the other hand, the two kinds of pastes A and B are measured in suitable amounts and are mixed together just before the repairing, and are applied onto the relining portion of the denture and/or onto the alveolar model. The denture and the alveolar model are then adhered together with force and are held until the pastes are sufficiently cured. After being cured, the denture is taken out from the alveolar model, and excess portions are removed by cutting.

The repairing method using the dental soft relining material (II) of the present invention can be roughly divided into two depending upon the case of when the old denture is to be relined and the case of preparing a new denture relined with the soft material. When the old denture is to be relined, the portion to be relined with the soft relining material is cut off. Then, the pastes are applied onto the relining portion of the denture and/or onto the alveolar model. The denture and the alveolar model are then adhered together with force, and are, as required, packed in a flask which is then heated in a hot bath, by the dry heating or by the irradiation with electromagnetic waves to cure the soft relining material. After being cured, the denture is taken out from the alveolar model and excess portions are removed by cutting. A new denture relined with the soft material is prepared as described below. That is, a spacer is fitted to a portion to be relined with the soft material thereby to prepare a denture in a flask, and a spacer portion is substituted by the soft relining material of the present invention after the resin for denture base has been cured. That is, after the spacer is removed, the pastes for the soft relining material of the present invention are charged, and the flask is fitted again, followed by heating in a hot bath, by the dry heating or by the irradiation with electromagnetic waves. Or, the soft relining material of the present invention is cured simultaneously with the curing of the resin for denture base, i.e, the spacer for the portion to be relined with soft material is removed under the condition where the resin for denture base is under the cake-like state. Then, the soft relining material is allowed to flow to charge the flask with the resin for denture base and with the soft relining material of the present invention, simultaneously, followed by heating and curing.

The dental soft relining material obtained according to the present invention exhibits a suitable degree of elasticity after curing, forms an elastic material having excellent resistance against coloring, and can be suitably used as a dental soft relining material having machinability.

EXAMPLES

The present invention will be described more concretely by way of embodiments. It should, however, be noted that the present invention is in no way limited thereto.

Table 1 shows unsaturated bond-containing silicones and Table 2 shows SiH siloxanes that are used in Examples and in Comparative Examples.

TABLE 1

Unsaturated bond-containing silicone $$H_2C=CHSiO(SiO)_l(SiO)_m(SiO)_nSiCH=CH_2$$

with side groups $CH_3, CH_3, CH_3, CH_3, CH_3$ (top) and $CH_3, CH_3, CH, Ph, CH_3$ (bottom), where CH connects to $CH_2$ via double bond.

| Compound No. | 1 | 2 | 3 | 4 | 5 |
|---|---|---|---|---|---|
| l | 200 | 1000 | 2000 | 1500 | 500 |
| m | 0 | 0 | 0 | 5 | 0 |
| n | 0 | 0 | 0 | 0 | 100 |

TABLE 2

| | SiH silicones | | | | |
|---|---|---|---|---|---|
| | $\text{RSiO}(\text{SiO})_x(\text{SiO})_y(\text{SiO})_z\text{SiR}$ with side groups $\text{CH}_3\text{CH}_3$, $\text{CH}_3\text{CH}_3$, $\text{CH}_3\text{H}$, $\text{CH}_3\text{Ph}$, $\text{CH}_3\text{CH}_3$ | | | | |
| Compound No. | 6 | 7 | 8 | 9 | 10 |
| R | CH₃ | CH₃ | CH₃ | H | H |
| x | 20 | 50 | 20 | 20 | 10 |
| y | 20 | 10 | 20 | 10 | 0 |
| z | 0 | 0 | 5 | 0 | 0 |

In Examples and Comparative Examples, the dental soft relining materials were evaluated by the methods described below, and the same samples were measured or evaluated three times and their average values were recorded.

(1) Shore hardness.

The pastes A and B of required amounts were mixed together, charged in a mold made of a polytetrafluoroethylene (hereinafter abbreviated as PTFE) having a hole 9 mm in diameter and 12 mm in length, and were sufficiently cured in the air at 37° C. After being cured, the paste was taken out from the mold, left to stand in the air at 37° C. for 24 hours and was measured for its hardness using a Shore A hardness tester.

(2) Tensile strength, elongation.

The pastes A and B of required amounts were mixed together, charged in a mold made of PTFE having a hole of the shape of a required dumbbell-shaped test piece and a thickness of 2 mm, and were sufficiently cured in the air at 37° C. After being cured, the paste was taken out from the mold, left to stand in the air at 37° C. for 24 hours and, then, the tensile strength and elongation at breakage were measured by using an autograph (manufactured by Shimazu Mfg. Co.) at a cross-head speed of 10 mm/min. The parallel portion of the dumbbell-shaped test piece possessed a size of 10 mm in length and 5 mm in width.

(3) Amount of coloring.

The pastes A and B of required amounts were mixed together, charged into a mold of PTFE measuring 10 mm×10 mm×2 mm, and were sufficiently cured in the air at 37° C. After being cured, the paste was taken out from the mold, left to stand in the air at 37° C. for 24 hours, and L*, a* and b* of before being colored were measured using a color-difference meter. Thereafter, the test piece was immersed in an aqueous solution containing curry in an amount of 20% by weight and was preserved at 40° C. for 24 hours with stirring. After being preserved, the test piece was washed with water, dried, and was measured again for its L*, a* and b* using the color-difference meter. The amount of coloring (ΔE*) was found from the differences ΔL*, Δa* and Δb* in compliance with the following equation, $$\Delta E^* = (\Delta L^{*2} + \Delta a^{*2} + \Delta b^{*2})^{1/2}$$

(4) Testing of machinability.

The pastes A and B of required amounts were mixed together, charged into a mold of PTFE having a hole 9 mm in diameter and 12 mm in length, and were sufficiently cured curing in the air at 37° C. After cured, the paste was taken out from the mold, left to stand in the air at 37° C. for 24 hours, and was evaluated for its machinability by using a micro-engine for dental use and by using a carbide bar and a silicone point. The evaluation was based upon the grades A to D in compliance with the following determination standards.

A—The surface is trimmed.

B—The edge portion is trimmed but the surface is not trimmed.

C—Not trimmed though scratched.

D—Not trimmed at all.

(Example 1)

Into a planetary were introduced a compound (1) and a compound (2) shown in Table 1 in an amount of 50 parts by weight, respectively, a vinyl siloxane complex of platinum in such an amount that platinum was 200 ppm with respect to the total amount of the compounds (1) and (2), and 200 parts by weight of fine particles of a polymethylsilsesquioxane having a grain size of 2 μm. These components were kneaded until the mixture became homogeneous to obtain a paste A.

Into the planetary were introduced the compound (1) and the compound (2) shown in Table 1 in an amount of 50 parts by weight, respectively, 4 parts by weight of a compound (6) shown in Table 2, and 100 parts by weight of fine particles of a polymethylsilsesquioxane having a grain size of 2 μm. These components were kneaded until the mixture became homogeneous to obtain a paste B.

The pastes A and B of these two kinds were mixed together at a mixing ratio of 1 to 1, and were evaluated in compliance with the above-mentioned evaluation method. The results were as shown in Table 4.

(Examples 2 to 11 and Comparative Examples 1 to 5)

The materials having compositions shown in Table 3 were kneaded using the planetary in the same manner as in Example 1 to prepare pastes. The platinum catalyst used was the same as the one used in Example 1.

By using these pastes, the testing was conducted in compliance with the above-mentioned evaluation method. The results were as shown in Table 4.

TABLE 3

| | Example 1 | Example 2 | Example 3 | Example 4 | Example 5 | Example 6 | Example 7 | Example 8 |
|---|---|---|---|---|---|---|---|---|
| Paste A | | | | | | | | |
| Unsaturated bond-containing silicone (parts by weight) | compound 1 (50) compound 2 (50) | compound 1 (100) | compound 2 (100) | compound 1 (100) | compound 1 (50) compound 2 (50) | compound 2 (100) | compound 4 (100) | compound 4 (100) |
| Platinum (ppm)* | 200 | 5 | 200 | 5 | 5 | 150 | 5 | 5 |
| Polyorganosilses- | oxane 1 | oxane 1 | oxane 1 | oxane 1 | oxane 1 | oxane 1 | oxane 1 | oxane 1 |

TABLE 3-continued

| | | | | | | | | |
|---|---|---|---|---|---|---|---|---|
| quioxane Ave. particles size (parts by weight) | 2 μm (100) | 0.5 μm (100) | 2 μm (60) | 2 μm (300) | 12 μm (100) | 2 μm (60) | 2 μm (10) | 4.5 μm (100) |
| Other fillers (parts by weight) | — | — | — | — | fumed silica (5) | — | — | — |
| Past B | | | | | | | | |
| Unsaturated bond-containing silicone (parts by weight) | compound 1 (50) compound 2 (50) | — | compound 2 (100) | compound 1 (100) | — | compound 2 (100) | compound 4 (100) | — |
| SiH silicone (parts by weight) | compound 6 (4) | compound 6 (100) | compound 6 (2) | compound 6 (9) | compound 6 (100) | compound 6 (2) compound 10 (2) | compound 7 (12) | compound 9 (100) |
| Polyorganosilsesquioxane Ave. particles size (parts by weight) | oxane 1 2 μm (100) | oxane 1 0.5 μm (100) | oxane 1 2 μm (60) | oxane 1 2 μm (300) | oxane 1 12 μm (100) | oxane 1 2 μm (60) | oxane 1 2 μm (10) | oxane 1 4.5 μm (100) |
| Other fillers (parts by weight) | — | — | — | — | fumed silica (5) | — | — | — |
| Mixing ratio (A/B) | 1/1 | 1/0.04 | 1/1 | 1/1 | 1/0.01 | 1/1 | 1/1 | 1/0.1 |
| H/V ratio** | 2 | 2 | 2 | 2 | 2 | 3 | 2 | 5 |

| | Example 9 | Example 10 | Example 11 | Comparative Example 1 | Comparative Example 2 | Comparative Example 3 | Comparative Example 4 | Comparative Example 5 |
|---|---|---|---|---|---|---|---|---|
| Paste A | | | | | | | | |
| Unsaturated bond-containing silicone (parts by weight) | compound 5 (100) | compound 1 (100) | compound 1 (100) | compound 1 (100) | compound 2 (100) | compound 1 (100) | compound 2 (100) | compound 1 (100) |
| Platinum (ppm)* | 5 | 5 | 100 | 5 | 5 | 5 | 5 | 5 |
| Polyorganosilsesquioxane Ave. particles size (parts by weight) | oxane 1 2 μm (100) | oxane 2 2 μm (100) | oxane 3 4.5 μm (100) | oxane 1 2 μm (100) | — | oxane 1 2 μm (2) | oxane 1 2 μm (100) | oxane 1 2 μm (400) |
| Other fillers (parts by weight) | — | — | — | — | fumed silica (30) | — | — | — |
| Past B | | | | | | | | |
| Unsaturated bond-containing silicone (parts by weight) | — | compound 1 (100) | — | — | — | — | — | — |
| SiH silicone (parts by weight) | compound 8 (100) | compound 7 (12) | compound 9 (100) | compound 9 (100) | compound 6 (100) | compound 6 (100) | compound 6 (100) | compound 6 (400) |
| Polyorganosilsesquioxane Ave. particles size (parts by weight) | oxane 1 2 μm (100) | oxane 2 2 μm (100) | oxane 3 4.5 μm (100) | oxane 1 2 μm (100) | — | oxane 1 2 μm (2) | oxane 1 2 μm (100) | oxane 1 2 μm (400) |
| Other fillers (parts by weight) | — | — | — | — | fumed silica (30) | — | — | — |
| Mixing ratio (A/B) | 1/0.01 | 1/1 | 1/0.02 | 1/0.14 | 1/0.01 | 1/0.04 | 1/0.001 | 1/0.04 |
| H/V ratio** | 2 | 2 | 2 | 2 | 2 | 2 | 0.2 | 2 |

*Reckoned as metal platinum with respect to unsaturated bond-containing silicone in the paste A.
**Number of hydrogen atoms bonded to silicon atoms per one unsaturated bond.
polyorganosilsesquioxane: oxane 1; polymethylsilsesquioxane, oxane 2; poly(50 mol % methyl + 50 mol % phenyl) silsesquioxane oxane 3; polyethylsilsesquioxane

TABLE 4

| | Shore A hardness | Tensile strength (kgf/cm²) | Elongation (%) | Amount of coloring with curry (ΔE ·) | Machinability |
|---|---|---|---|---|---|
| Example 1 | 58.5 | 23.2 | 360 | 5.3 | A |
| Example 2 | 60.3 | 20.8 | 270 | 9.5 | A |
| Example 3 | 38.2 | 16.8 | 620 | 4.3 | A |
| Example 4 | 68.3 | 27.8 | 160 | 6.7 | A |
| Example 5 | 60.2 | 24.5 | 380 | 7.0 | A |
| Example 6 | 37.8 | 18.1 | 600 | 5.2 | A |
| Example 7 | 37.1 | 11.0 | 190 | 4.5 | A |
| Example 8 | 60.3 | 22.0 | 240 | 7.5 | A |
| Example 9 | 51.0 | 21.5 | 490 | 10.1 | A |
| Example 10 | 58.8 | 21.1 | 390 | 6.0 | A |
| Example 11 | 59.6 | 21.8 | 270 | 6.8 | A |

TABLE 4-continued

|  | Shore A hardness | Tensile strength (kgf/cm$^2$) | Elongation (%) | Amount of coloring with curry ($\Delta E \cdot$ ) | Machinability |
|---|---|---|---|---|---|
| Comp. Example 1 | * | * | * | * | * |
| Comp. Example 2 | 60.5 | 25.3 | 280 | 18.9 | D |
| Comp. Example 3 | 32.1 | 4.2 | 130 | 4.6 | *** |
| Comp. Example 4 | * | * | * | * | * |
| Comp. Example 5 | ** | ** | ** | ** | ** |

*not measurable (not cured)
**not measurable (paste was not formed)
***brittle and collapsed It will be understood from the results of Table 4 that the dental soft relining materials (Examples 1 to 11) of the present invention exhibit suitable degrees of hardness, sufficient tensile strengths and elongations, small amounts of coloring and favorable machinability. According to Comparative Examples, on the other hand, the paste is not cured when the number of hydrogen atoms bonded to silicon atoms in the component (B) is smaller than three (Comparative Example 1), the amount of coloring is large and no machinability is obtained when the particles of a polyorganosilsesquioxane is not used as a filler (Comparative Example 2), sufficient mechanical strength is not obtained when the amount of the particles of a polyorganosilsesquioxane is smaller than 5 parts by weight (Comparative Example 3), the paste is not fully cured when the number of hydrogen atoms bonded to silicon atoms in the component (B) is smaller than 0.5 per one unsaturated bond in the component (A) (Comparative Example 4), and the paste is not formed when the amount of the particles of a polyorganosilsesquioxane is larger than 300 parts by weight (Comparative Example 5). Thus, the dental soft relining materials fail to exhibit good properties in all of the Comparative Examples.

The organopolysiloxane shown in Table 5 were used in the following Examples 12 to 18 and Comparative Examples 6 to 9.

TABLE 5

Component (E) — organopolysiloxane $$\text{RSiO(SiO)}_l\text{(SiO)}_m\text{(SiO)}_n\text{SiR}$$
with substituents CH$_3$, CH$_3$, CH$_3$, CH$_3$, CH$_3$ on the main chain silicons, and CH$_3$, CH$_3$, CH=CH$_2$, Ph, CH$_3$ as the other substituents.

| Compound No. | 11 | 12 | 13 | 14 |
|---|---|---|---|---|
| R | CH=CH$_2$ | CH=CH$_2$ | CH=CH$_2$ | CH$_3$ |

TABLE 5-continued

Component (E) — organopolysiloxane

| Compound No. | 11 | 12 | 13 | 14 |
|---|---|---|---|---|
| l | 200 | 1000 | 1500 | 1000 |
| m | 0 | 0 | 5 | 10 |
| n | 0 | 0 | 0 | 100 |

(Example 12)

Into the planetary were introduced 100 parts by weight of a compound (11) shown in Table 5, 2 parts by weight of a benzoyl peroxide (hereinafter abbreviated as BPO) as an organic peroxide catalyst, and 100 parts by weight of the polymethylsilsesquioxane having a grain size of 2 μm. These components were kneaded together until the mixture became homogeneous thereby to obtain a sample paste. The sample paste was charged into a required mold, secured by a clamp via a glass plate, and was immersed in the boiling water for one hour. The paste was then taken out, left to stand in the air at 37° C. for 24 hours and was measured for its physical properties in compliance with the aforementioned testing method. The results were as shown in Table 3.

(Examples 13 to 18 and Comparative Examples 6 to 9)

The materials of compositions shown in Table 6 were kneaded by using a kneader to prepare pastes. By using these pastes, cured products were obtained and were tested in compliance with the aforementioned evaluation method. The results were as shown in Table 7.

TABLE 6

|  | Example 12 | Example 13 | Example 14 | Example 15 | Example 16 | Example 17 | Example 18 | Comparative Example 6 |
|---|---|---|---|---|---|---|---|---|
| Organo-poly-siloxane (parts by weight) | compound 11 (100) | compound 11 (100) | compound 11 (100) | compound 11 (50) compound 12 (50) | compound 12 (100) | compound 13 (100) | compound 14 (100) | compound 11 (100) |
| Organic peroxide | BPO (2) | BPO (2) | BPO (2) | DCPO (5) | DCPO (5) | BPO (5) | BPO (2) | BPO (2) |

TABLE 6-continued

| (parts by weight) | | | | | | | | |
|---|---|---|---|---|---|---|---|---|
| polyorgano-silsesquioxane Ave. particles size (parts by weight) | oxane 1 2 μm (100) | oxane 1 0.5 μm (100) | oxane 1 2 μm (50) | oxane 1 12 μm (300) | oxane 2 2 μm (100) | oxane 1 4.5 μm (100) | oxane 3 2 μm (5) | — |
| Other fillers (parts by weight) | — | — | — | — | fumed silica (5) | — | — | fumed silica (30) |
| Curing condition | 100° C. 1 Hr in water | 100° C. 1 Hr in water | 100° C. 1 Hr in air | 120° C. 1 Hr in air | 120° C. 1 Hr in air | 100° C. 1 Hr in water | 100° C. 1 Hr in water | 100° C. 1 Hr in air |

| | Comparative Example 7 | Comparative Example 8 | Comparative Example 9 |
|---|---|---|---|
| Organopolysiloxane (parts by weight) | compound 11 (100) | compound 11 (100) | compound 11 (100) |
| Organic peroxide (parts by weight) | BPO (2) | BPO (0.01) | BPO (2) |
| polyorganosilsesquioxane Ave. particles size (parts by weight) | oxane 1 2 μm (2) | oxane 1 2 μm (100) | oxane 1 2 μm (350) |
| Other fillers (parts by weight) | — | — | — |
| Curing condition | 100° C. 1 Hr in water | 100° C. 1 Hr in water | 100° C. 1 Hr in water |

Organic peroxide DCPO: dicumyl peroxide
Polyorganosilsesquioxane:
oxane 1; polymethylsilsesquioxane
oxane 2; poly(50 mol % methyl + 50 mol % phenyl) silsesquioxane

TABLE 7

| | Shore A hardness | Tensile strength (kgf/cm$^2$) | Elongation (%) | Amount of coloring with curry (ΔE · ) | Machinability |
|---|---|---|---|---|---|
| Example 12 | 58.0 | 23.3 | 380 | 6.1 | A |
| Example 13 | 61.1 | 25.6 | 290 | 7.0 | A |
| Example 14 | 54.2 | 19.6 | 300 | 5.8 | A |
| Example 15 | 62.1 | 33.0 | 160 | 6.9 | A |
| Example 16 | 55.0 | 28.5 | 510 | 7.8 | A |
| Example 17 | 57.9 | 25.1 | 330 | 6.3 | A |
| Example 18 | 40.0 | 18.9 | 360 | 4.7 | A |
| Comp. Example 6 | 60.5 | 25.1 | 430 | 16.9 | D |
| Comp. Example 7 | 32.5 | 4.1 | 150 | 4.5 | *** |
| Comp. Example 8 | * | * | * | * | * |
| Comp. Example 9 | ** | ** | ** | ** | ** |

*not measurable (not cured)
**not measurable (paste was not formed)
***brittle and collapsed

We claim:

1. A method of repairing a denture comprising applying a dental soft relining material containing:

(A) 100 parts by weight of an organopolysiloxane having in a molecule thereof at least two organic groups with a terminal unsaturated bond;

(B) an organohydrogenpolysiloxane having in a molecule thereof at least three hydrogen atoms bonded to silicon atoms, in such an amount that the number of said hydrogen atoms is 0.5 or greater per one unsaturated bond in the component (A);

(C) a platinum catalyst in an amount of 0.1 to 1000 ppm reckoned as platinum atoms with respect to the total amount of the component (A) and the component (B); and (D) 5 to 300 parts by weight of a fine particle of a polyorganosilsesquioxane to the mucosa surface of the denture and/or an alveolar model, adhering said denture to the residual ridge or the alveolar model with force, and then curing the soft relining material.

2. A method of repairing a denture according to claim 1, wherein the organic groups bonded to silicon atoms of the organopolysiloxane (A) are an organic group having a terminal unsaturated bond and a methyl group, said organopolysiloxane having in a molecule thereof at least two organic groups with a terminal unsaturated bond.

3. A method of repairing a denture according to claim 1 or 2, wherein the organic group having a terminal unsaturated bond is a vinyl group.

4. A method of repairing a denture according to claim 1, wherein the organic groups bonded to silicon atoms of the organohydrogenpolysiloxane (B) are a hydrogen atom and a methyl group, said organohydrogenpolysiloxane having in a molecule thereof at least three hydrogen atoms bonded to silicon atoms.

5. A method of repairing a denture according to claim 1, wherein the organopolysiloxane (A) having in a molecule thereof at least two organic groups with a terminal unsaturated bond is blended with the organohydrogenpolysiloxane (B) that has in a molecule thereof at least three hydrogen atoms bonded to silicon atoms in such an amount that the number of the hydrogen atoms is from 1 to 5 per one unsaturated bond in the component (A).

6. A method of repairing a denture according to claim 1, wherein a platinum catalyst is a vinylsiloxane platinum complex.

7. A method of repairing a denture according to claim 1, wherein the fine particle of a polyorganosilsesquioxane (D) has an average grain size of from 0.1 to 100 μm.

8. A method of repairing a denture according to claim 7, wherein the fine particle of a polyorganosilsesquioxane (D) is a fine particle of a polymethylsilsequioxane.

9. A method of repairing a denture comprising applying a dental soft relining material containing:

(E) 100 parts by weight of an organopolysiloxane;

(F) 0.05 to 15 parts by weight of an organic peroxide; and (D) 5 to 300 parts by weight of a fine particle of a polyorganosilsesquioxane; onto the mucosa surface of the denture and/or onto an alveolar model, and then adhering said denture to the alveolar model with force followed by heat-curing.

10. A method of repairing a denture according to claim 9, wherein the organic groups bonded to silicon atoms of the organopolysiloxane (E) are a methyl group and a vinyl group.

11. A method of repairing a denture according to claim 9 or 10, wherein the organopolysiloxane (E) has a siloxy unit (average polymerization degree) of from 50 to 5000.

12. A method of repairing a denture according to claim 9, wherein the fine particle of a polyorganosilsesquioxane (D) has an average grain size of from 0.1 to 100 μm.

13. A method of repairing a denture according to claim 12, wherein the fine particle of a polyorganosilsesquioxane (D) is a fine particle of a polymethylsilsesquioxane.

14. A denture comprising a denture and a layer of a soft relining material provided on the side of the mucosa surface of said denture, wherein said soft relining material comprises a cured product of a composition which contains:

(A) 100 parts by weight of an organopolysiloxane having in a molecule thereof at least two organic groups with a terminal unsaturated bond;

(B) an organohydrogenpolysiloxane having in a molecule thereof at least three hydrogen atoms bonded to silicon atoms, in such an amount that the number of said hydrogen atoms is 0.5 or greater per one unsaturated bond in the component (A);

(C) a platinum catalyst in an amount of 0.1 to 1000 ppm reckoned as platinum atoms with respect to the total amount of the component (A) and the component (B); and (D) 5 to 900 parts by weight of a fine particle of a polyorganosilsesquioxane.

15. A denture comprising a denture and a layer of a soft relining material provided on the side of the mucosa surface of said denture, wherein said soft relining material comprises a cured product of a composition which contains:

(E) 100 parts by weight of an organopolysiloxane;

(F) 0.05 to 15 parts by weight of an organic peroxide; and (D) 5 to 300 parts by weight of a fine particle of a polyorganosilsesquioxane.

16. A method of repairing a denture with a dental soft relining material which comprises removing a portion of the denture to thereby expose a new surface to be relined with the dental soft relining material, applying to the exposed surface a dental soft relining material comprising:

(A) 100 parts by weight of an organopolysiloxane having in a molecule thereof at least two organic groups with a terminal unsaturated bond;

(B) an organohydrogenpolysiloxane having in a molecule thereof at least three hydrogen atoms bonded to silicon atoms, in such an amount that the number of said hydrogen atoms is 0.5 or greater per one unsaturated bond in the component (A);

(C) a platinum catalyst in an amount of 0.1 to 1000 ppm, measured as platinum atoms, with respect to the total amount of the component (A) and the component (B); and (D) 5 to 300 parts by weight of a fine particles of a polyorganosilsesquioxane, fitting the denture with relining material into the oral cavity of a patient, allowing the applied dental soft relining material to cure, and removing the denture with cured relining material from the oral cavity.

17. A method according to claim 16 which further comprises removing excess portions of the cured relining material by cutting same.

* * * * *